United States Patent [19]

Oba et al.

[11] Patent Number: 4,500,719

[45] Date of Patent: Feb. 19, 1985

[54] PROCESS FOR THE PREPARATION OF N-ALKENYLPHENYLMALEIMIDES AND N,N'-[ALKENYLENEPHENYLENE]BIS-MALEMIDES

[75] Inventors: Masayuki Oba, Tokyo; Motoo Kawamata, Yokohama; Hikotada Tsuboi, Yokohama; Nobuhito Koga, Yokohama, all of Japan

[73] Assignee: Mitsui Toatsu Chemicals, Incorporated, Tokyo, Japan

[21] Appl. No.: 408,042

[22] Filed: Aug. 13, 1982

Related U.S. Application Data

[62] Division of Ser. No. 131,804, Mar. 19, 1980, Pat. No. 4,376,206.

[51] Int. Cl.³ .............................. C07D 207/40
[52] U.S. Cl. .................... 548/522; 548/521; 548/549
[58] Field of Search .................... 548/548, 549, 546

[56] References Cited

U.S. PATENT DOCUMENTS 2,444,536  7/1948  Searle ................................. 548/549
4,172,836  10/1979  Baumann et al. ................... 548/546

FOREIGN PATENT DOCUMENTS 56-131566  10/1981  Japan ................................. 548/549
56-145272  11/1981  Japan ................................. 548/547

*Primary Examiner*—Glennon H. Hollrah
*Assistant Examiner*—D. B. Springer
*Attorney, Agent, or Firm*—Fisher, Christen & Sabol

[57] ABSTRACT

Disclosed are novel alkenylphenylmaleimide derivatives having the general formula

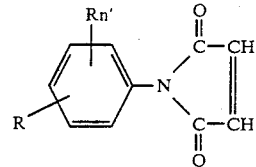

where R is an alkenyl radical of from 3 to 12 carbon atoms, R' is a hydrogen atom, a halogen atom, or a straight-chain or branched alkyl radical of from 1 to 4 carbon atoms, and n is a whole number of from 1 to 4, and linear dimers thereof as well as a process for the preparation of such maleimide compounds.

20 Claims, No Drawings

PROCESS FOR THE PREPARATION OF N-ALKENYLPHENYLMALEIMIDES AND N,N'-[ALKENYLENEPHENYLENE]BISMALE-MIDES

This is a division of application Ser. No. 131,804, filed Mar. 19, 1980 now U.S. Pat. No. 4,376,206 issued Mar. 8, 1983.

BACKGROUND OF THE INVENTION

(1) Field of the Invention

This invention relates to novel alkenylphenylmaleimide derivatives and linear dimers thereof which have high thermal decomposition temperatures, exhibit rapid curability, and are easily soluble in common organic solvents. In another aspect, it relates to a process for the preparation of such maleimide compounds.

(2) Description of the Prior Art

A variety of heat resistant resins have been developed as insulating materials meeting the constant demands for greater capacity, miniaturization and weight-saving, improved reliability and thermal stability, longer lifetime, maintenance-free properties, etc. of electronic devices and apparatus. Generally, bismaleimides (including N,N'-(methylenedi-p-phenylene)bismaleimide as a typical example) obtained by reacting a primary amine with maleic anhydride provide thermosetting resins having excellent heat resistance and a dense structure. However, these maleimides are high in melting point and sparingly soluble in common organic solvents. Accordingly, if it is desired to use them in the form of a solution, they must be dissolved in high-boiling polar organic solvents, such as dimethylformamide, dimethylacetamide, N-methylpyrrolidone, dimethyl sulfoxide, etc., that are undesirable for reasons of safety and health. Moreover, when an impregnating varnish prepared by reacting such a bismaleimide with a diamine and dissolving the resulting prepolymer in dimethylformamide or N-methylpyrrolidone is used in the fabrication of copper-clad laminates, removal of the solvent is so difficult that gas bubbles, blisters of the copper foil, and other defects may develop. Because of this great technical disadvantage, the needs of the times have recently changed from impregnating varnishes of the solution type to ones of the solventless type. In order to solve the above-described problems, there have been proposed, for example, a method of modifying poly(phenylmethylene)polymaleimide by incorporating an poxy resin thereinto (Japanese Patent Laid-open No. 21098/'75) and a method of modifying a prepolymer of a bismaleimide and a polyamine by incorporating an epoxy resin thereinto (Japanese Patent Publication No. 27519/'75). In these modified maleimide compositions, however, the maleimide tends to precipitate at temperatures in the vicinity of room temperature and the limitation placed on the maleimide content prevents the achievement of satisfactory heat resistance and adhesion properties. Thus, they are not suitable for practical use as industrial materials required to have high performance.

In the prior art, processes for preparing maleimides, bismaleimides, and polymaleimides are well known and one example thereof is disclosed in U.S. Pat. No. 4,130,564. However, the maleimide compounds of the present invention cannot satisfactorily be prepared according to this process. Specifically, since the maleimide compounds of the present invention have high solubility in organic solvents and great affinity for organic solvents, they cannot sufficiently be crystallized by cooling the reaction mixture after completion of the maleimide-forming reaction. Moreover, if a bad solvent such as water or the like is used to precipitate the formed maleimide compound (alkenylphenylmaleimide derivative or linear dimer thereof) from the reaction mixture, the maleimide compound undergoes a marked degree of agglomeration and fails to remain in the form of particles of proper size. Furthermore, the maleimide compound precipitated by a large amount of bad solvent is a very impure product containing various by-products and must therefore be purified by recrystallization from a special organic solvent such as acetonitrile or the like. Thus, the prior art fails to provide a technologically simple and industrially advantageous process for preparing the maleimide compounds of the present invention.

SUMMARY OF THE INVENTION

It is an object of the present invention to provide novel alkenylphenylmaleimide derivatives and linear dimers thereof.

It is another object of the present invention to provide novel alkenylphenylmaleimide derivatives and linear dimers thereof which are easily soluble in common organic solvents, have high thermal decomposition temperatures, and exhibit such properties as rapid curability, homopolymerizability, and the like.

It is a further object of the present invention to provide novel alkenylphenylmaleimide derivatives and linear dimers thereof which can give thermosetting resins having excellent electrical properties, mechanical properties, and thermal stability and which are useful in various other applications.

It is a still further object of the present invention to provide a process for the preparation of such novel alkenylphenylmaleimide derivatives and linear dimers thereof.

DETAILED DESCRIPTION OF THE INVENTION

According to the present invention, there are provided alkenylphenylmaleimide derivatives having the general formula

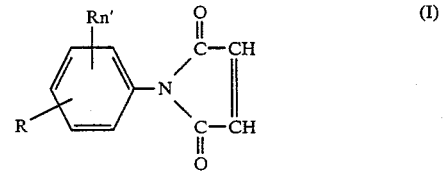

where R is an alkenyl radical of from 3 to 12 carbon atoms, R' is a hydrogen atom, a halogen atom, or a straight-chain or branched alkyl radical of from 1 to 4 carbon atoms, and n is a whole number of from 1 to 4, and linear dimers of like or different alkenylphenylmaleimide derivatives having the general formula

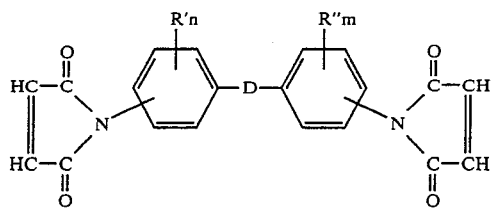

where R' and R" are hydrogen atoms, halogen atoms, or alkyl radicals of from 1 to 4 carbon atoms, n and m are whole numbers of from 1 to 4, and D is a divalent organic radical of from 6 to 24 carbon atoms containing a carbon-to-carbon double bond.

The maleimide compounds of the present invention, which have lower melting points than prior art maleimides, are useful as impregnating varnishes of the solventless type. In addition, the maleimide compounds of the present invention have such rapid curability that the energy required for the production of various materials can be saved greatly. Moreover, owing to the reactive double bonds present in the molecule, the maleimide compounds of the present invention cannot only homopolymerize but can also react readily with other compounds to form a variety of curable resins. Furthermore, their high thermal decomposition temperature permit the formation of resins having excellent thermal stability and their high solubilities in common organic solvents bring about an enhancement in operating efficiency.

By way of example, the melting points and thermal decomposition temperatures of two typical maleimide compounds of the present invention are shown in Table 1, and the solubilities of one typical maleimide compound of the present invention in several organic solvents are shown in Table 2. The thermal decomposition temperatures were measured in a stream of nitrogen gas by means of a thermobalance heated at a rate of 10° C. per minutes.

TABLE 2

| Solubilities of N—p-isopropenylphenylmaleimide | |
|---|---|
| Organic Solvent | Solubility (at room temperature) |
| Dimethylformamide | 46.5 wt. % or higher |
| Dioxane | 41.5 wt. % |
| Tetrahydrofuran | 41.0 wt. % |
| Chloroform | 30.0 wt. % |
| Acetone | 23.3 wt. % |
| Methyl ethyl ketone | 21.7 wt. % |

Typical examples of the novel maleimide compounds represented by the general formulas (I) and (II) include
N-(o-isopropenylphenyl)maleimide,
N-(m-isopropenylphenyl)maleimide,
N-(p-isopropenylphenyl)maleimide,
N-(3-methyl-4-isopropenylphenyl)maleimide,
N-(3-chloro-4-isopropenylphenyl)maleimide,
N-[p-(1-ethylethenyl)phenyl]maleimide,
N-[p-(1-methyl-1-propenyl)phenyl]maleimide,
N-[2-methyl-4-(1'-methyl-1'-propenyl)phenyl]maleimide,
N-[p-(1-propylethenyl)phenyl]maleimide,
N-[p-(1-methyl-1-butenyl)phenyl]maleimide,
N-[3-chloro-4-(1'-methyl-1'-propenyl)phenyl]maleimide,
N,N'-(1-methylene-3,3-dimethyltrimethylenedi-p-phenylene)bismaleimide,
N,N'-(1-methyl-3,3-dimethyl-1-propenylenedi-p-phenylene)bismaleimide,
N,N'-[1-methylene-3,3-dimethyltrimethylenebis(3'-methyl-1',4'-phenylene)]bismaleimide,
N,N'-[1-methyl-3,3-dimethyl-1-propenylenebis(3'-methyl-1',4'-phenylene)]bismaleimide,
N,N'-(1-methylene-3,3-diethyltrimethylenedi-p-phenylene)bismaleimide,
N,N'-[1-methylene-3,3-diethyltrimethylenebis(3'-chloro-1',4'-phenylene)bismaleimide,
N,N'-(1-methyl-3,3-dipropyl-1-propenylenedi-p-phenylene)bismaleimide,
and the like.

TABLE 1

Melting Points and Thermal Decomposition Temperatures of Maleimide Compounds

| Maleimide Compound | Melting Point (°C.) | Thermal Decomposition Temperature* (°C.) |
|---|---|---|
| N—p-isopropenylphenylmaleimide | 109–117 | 445 |
| N,N'—(1-methyl-3,3-dimethyl-1-propenylenedi-p-phenylene)-bismaleimide | 99–110 | 443 |

*The temperature at which a 5% loss in weight is caused.

The above-described maleimide compounds of the present invention can be prepared by effecting reaction of an alkenylphenylmaleamic acid derivative having the general formula

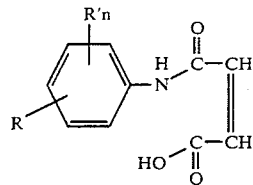
(III)

where R is an alkenyl radical of from 3 to 12 carbon atoms, R' is a hydrogen atom, a halogen atom, or a straight-chain or branched alkyl radical of from 1 to 4 carbon atoms, and n is a whole number of from 1 to 4, or a linear dimer of like or different alkenylphenylmaleamic acid derivatives having the general formula

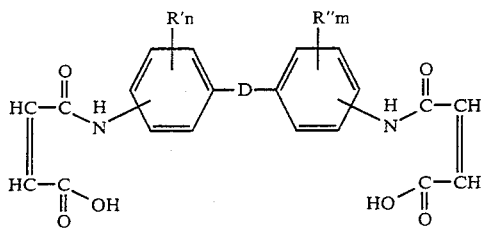
(IV)

where R' and R'' are hydrogen atoms, halogen atoms, or straight-chain or branched alkyl radicals of from 1 to 4 carbon atoms, n and m are whole numbers of from 1 to 4, and D is a divalent organic radical of from 6 to 24 carbon atoms containing a carbon-to-carbon double bond, with a dehydrating agent in the presence of an organic solvent, a catalyst, and a tertiary amine; and then adding an alcohol to the reaction mixture.

Typical examples of the alkenylphenylmaleamic acid derivative represented by the general formula (III) include
N-(o-isopropenylphenyl)maleamic acid,
N-(m-isopropenylphenyl)maleamic acid,
N-(p-isopropenylphenyl)maleamic acid,
N-(2-methyl-4-isopropenylphenyl)maleamic acid,
N-(3-methyl-4-isopropenylphenyl)maleamic acid,
N-(2-chloro-4-isopropenylphenyl)maleamic acid,
N-(2-bromo-4-isopropenylphenyl)maleamic acid,
N-(3-chloro-4-isopropenylphenyl)maleamic acid,
N-(3-bromo-4-isopropenylphenyl)maleamic acid,
N-[o-(1-ethylethenyl)phenyl]maleamic acid,
N-[p-(1-ethylethenyl)phenyl]maleamic acid,
N-[o-(1-methyl-1-propenyl)phenyl]maleamic acid,
N-[p-(1-methyl-1-propenyl)phenyl]maleamic acid,
N-[2-methyl-4-(1'-methyl-1'-propenyl)phenyl]maleamic acid,
N-[2-chloro-4-(1'-methyl-1'-propenyl)phenyl]maleamic acid,
N-[2-bromo-4-(1'-methyl-1'-propenyl)phenyl]maleamic acid, and the like. The linear dimer of like or different alkenylphenylmaleamic acid derivatives represented by the general formula (IV) is a bismaleamic acid consisting of a dimerization product as described above, and typical examples thereof include N,N'-(1-methylene-3,3-dimethyltrimethylenedi-p-phenylene)bismaleamic acid,
N,N'-(1-methyl-3,3-dimethyl-1-propylenedi-p-phenylene)bismaleamic acid,
N,N'-[1-methylene-3,3-dimethyltrimethylenebis(3'-methyl-1',4'-phenylene)]bismaleamic acid,
N,N'-[1-methyl-3,3-dimethyl-1-propenylenebis(3'-methyl-1',4'-phenylene)]bismaleamic acid,
N,N'-[1-methylene-3,3-dimethyltrimethylenebis(3'-chloro-1',4'-phenylene)]bismaleamic acid,
N,N'-(1-methylene-3,3-diethyltrimethylenedi-p-phenylene)-bismaleamic acid,
N,N'-[1-methylene-3,3-diethyltrimethylenebis(3'-chloro-1',4'-phenylene)]bismaleamic acid,
and the like.

The compounds of formulas (III) and (IV) can be prepared by effecting reaction of an alkenylaniline derivative having the general formula

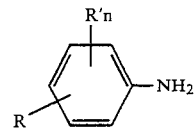

where R is an alkenyl radical of from 3 to 12 carbon atoms, R' is a hydrogen atom, a halogen atom, or a straight-chain or branched alkyl radical of from 1 to 4 carbon atoms, and n is a whole number of from 1 to 4, or a linear dimer thereof with maleic anhydride at a temperature of from 10° to 40° C. in an organic solvent such as acetone or the like. In order to carry out the process of the present invention to advantage, the resulting organic solvent solution of the alkenylphenylmaleamic acid derivative or linear dimer thereof may be directly used for the cyclodehydration reaction of the present invention without being subjected to any separation step.

The organic solvent which is used in the process of the present invention is selected from the group consisting of halogenated hydrocarbons such as chloroform, methylene chloride, carbon tetrachloride, trichloroethylene, etc.; ketones such as acetone, methyl ethyl ketone, cyclohexanone, etc.; organic carboxylic acids and esters thereof such as formic acid, acetic acid, butyric acid, methyl acetate, ethyl acetate, etc.; alcohols and ethers such as methyl alcohol, ethyl alcohol, propyl alcohol, ether, dioxane, tetrahydrofuran, cellosolve, methyl cellosolve, etc.; alicyclic and aromatic hydrocarbons such as cyclohexane, benzene, toluene, xylene (o-, m-, and p-isomers), mesitylene, etc.; aromatic compounds such as chlorobenzene, cresol (o-, m-, and p-isomers), dichlorobenzene (o-, m-, and p-isomers), etc.; nitrogen-containing and sulfur-containing compounds such as acetonitrile, pyridine, N,N-dimethylacetamide, N,N-dimethylformamide, hexamethylphosphoramide, N-methyl-2-pyrrolidone, N-methylcaprolactam, dimethyl sulfoxide, etc.; and the like. Among them, acetone, methyl ethyl ketone, acetonitrile, tetrahydrofuran, and N,N-dimethylformamide are particularly preferred. These organic solvents may be used alone or in combination. The amount of organic solvent used is preferably from 1.1 to 80 times the weight of the alkenylaniline derivative, or linear dimers thereof used as the starting material.

The catalyst which is used for the cyclodehydration reaction in the process of the present invention is selected from the group consisting of hydrated or unhydrated inorganic acid salts, organic acid salts, and halides of sodium, potassium, lithium, iron, nickel, cobalt, copper, and manganese as well as acetylacetone complexes of the foregoing metals. Typical examples of the catalyst include the hydrated or unhydrated hydrogen carbonate, carbonate, sulfate, nitrate, phosphate, pyrophosphate, acetate, and butyrate of sodium; the hydrated or unhydrated hydrogen carbonate, carbonate, sulfate, nitrate, phosphate, pyrophosphate, acetate, and butyrate of potassium; the hydrated or unhydrated hydrogen carbonate, carbonate, sulfate, nitrate, phosphate, pyrophosphate, chloride, bromide, iodide, acetate, and butyrate of lithium; the hydrated or unhydrated carbonate, sulfate, phosphate, chloride, bromide, iodide, formate, acetate, butyrate, stearte, and naphthenate of iron (II or III); the hydrated or unhydrated carbonate, sulfate, phosphate, chloride, bromide, iodide, formate, acetate, butyrate, stearate, and naphthenate of nickel (II); the hydrated or unhydrated carbonate, sulfate, phosphate, chloride, bromide, iodide, formate, acetate, butyrate, stearate, and naphthenate of cobalt (II or (III); the hydrate or unhydrated carbonate, sulfate, phosphate, chloride, bromide, iodide, formate, acetate, butyrate, stearate, and naphthenate of copper (I or II); the hydrated or unhydrated carbonate, sulfate, phosphate, chloride, bromide, iodide, formate, acetate, butyrate, stearate, and naphthenate of manganese (II or III); the acetylacetone complexes of copper (I or II), nickel (II), cobalt (II or III), and manganese (II or III); and the like. In order to achieve a satisfactory effect, these catalysts may be used alone or in combination. Among them, hydrated or unhydrated sodium acetate, nickel (II) acetate, and cobalt(II) acetate are particularly preferred. The amount of catalyst used is in this range of from 0.001 to 1.2 moles and preferably from 0.002 to 0.5 mole per mole of the alkenylphenylmaleamic acid derivative or linear dimer thereof. If the amount of catalyst used is less than 0.001 mole, the reaction rate is so low that the cyclodehydration reaction requires an unduly long time, while if it is greater than 1.2 moles, undesirable side reactions take place and thereby reduces the yield of the desired alkenylphenylmaleimide derivative or linear dimer thereof.

The tertiary amine which is used in the process of the present invention is selected from the group consisting of trialkylamines having alkyl radicals of from 3 to 20 carbon atoms (for example, trimethylamine, triethylamine, tributylamine, etc.), N,N-diethylcyclohexylamine, N,N-dimethylbenzylamine, N-methylpiperidine, 1,4-diazabicyclo[2.2.2]octane, 1,8-diazabicyclo[5.4.0]7-undecene, N-methylmorpholine, and the like. These tertiary amines may be used alone or in combination. Among them, triethylamine is particularly preferred. The amount of tertiary amine used is in the range of from 0.01 to 1.1 moles and preferably from 0.05 to 0.6 mole per mole of the alkenylphenylmaleamic acid derivative or linear dimer thereof.

The dehydrating agent which is used in the process of the present invention can be any compound that acts on the maleamic acid group of the alkenylphenylmaleamic acid derivative or linear dimer thereof to convert it to the maleimido group and, per se, undergoes hydration or hydrolysis or any compound that has very strong dehydrating power. Typical inorganic dehydrating agents include phosphorus pentoxide, orthophosphoric acid, pyrophosphoric acid, condensed phosphoric acid, sulfuric anhydride, sulfuric acid, sodium sulfate, calcium oxide, barium oxide, and the like, and typical organic dehydrating agents include carboxylic acid anhydrides such as acetic anhydride, propionic anhydride, butyric anhydride, valeric anhydride, succinic anhydride, glutaric anhydride, benzoic anhydride, phthalic anhydride, and the like. These dehydrating agents may be used alone or in combination. Among them, acetic anhydride is particularly preferred because it is easy to handle and permits simple after-treatment following the cyclodehydration reaction. The amount of dehydrating agent used is in the range of from 0.2 to 3 moles and preferably from 0.3 to 2 moles per equivalent of the maleamic acid group of the alkenylphenylmaleamic acid derivative or linear dimer thereof.

In carrying out the process of the present invention, the catalyst, the tertiary amine, and the dehydrating agent may be added in any desired order. However, it is preferable to add the catalyst, the tertiary amine, and the dehydrating agent in that order. If an inorganic compound such as phosphorus pentoxide, orthophosphoric acid, pyrophosphoric acid, condensed phosphoric acid, sulfuric anhydride, sulfuric acid, calcium oxide, barium oxide, or the like is used as the dehydrating agent, the cyclodehydration reaction proceeds without using any particular catalyst or tertiary amine. Moreover, dehydrating agents such as condensed phosphoric acid, sulfuric acid, acetic anhydride, and the like can also serve as solvents, though it is preferable to carry out the cyclodehydration reaction in the presence of an organic solvent.

The reaction temperature at which the alkenylphenylmaleamic acid derivative or linear dimer thereof undergoes cyclodehydration to form the corresponding maleimide is in the range of from 0° to 120° C. and preferable from 30° to 80° C. The reaction time depends on the concentrations of catalyst and tertiary amine used, the reaction temperature, and the like, but is in the range of from 0.5 to 9 hours and preferably from 2 to 5 hours. The cyclodehydration reaction of the present invention can proceed under any pressure that maintains the reaction system in the liquid state.

After the cyclodehydration reaction is completed under the above-described reaction conditions, the reaction mixture is cooled. As a result, it is obtained in the form of a homogeneous solution or a slurry (when the organic solvent is used in small amounts). Then, the desired alkenylphenylmaleimide derivative or linear dimer thereof (hereinafter referred to as the maleimide compound) is precipitated either by adding a precipitant (for example, water) slowly to the reaction mixture or by adding the reaction mixture dropwise to a precipitant.

However, the maleimide compound thus obtained is tarry because of its great affinity for the organic solvent. Accordingly, when water is used as the precipitant, an alcohol is added to the homogeneous reaction mixture after completion of the maleimide-forming reaction in order that the maleimide compound may be uniformly dispersed in water and the precipitate may be obtained in the form of particles of proper size. Typical examples of the alcohol used for this purpose include methyl alcohol, ethyl alcohol, 1-propyl alcohol, 2-propyl alcohol, 1-butyl alcohol, 2-butyl alcohol, tert-butyl alcohol, and the like. The amount of alcohol used is in the range of from 0.05 to 200 g and preferably from 1.0 to 50 g per 100 g of the reaction mixture. If the amount of alcohol used is less than 0.05 g, the maleimide compound becomes tarry, while if it is greater than 250 g, the maleimide compound form colloidal particles which can hardly be separated by filtration. No special limitation is placed on the temperature at which the addition of an alcohol is carried out, though the preferred temperature range is from 5° to 40° C. The reaction mixture having an alcohol added thereto gives a sufficiently pure maleimide compound in the form of particles of proper size either by adding a precipitant thereto or by adding it to a precipitant. The precipitant used for this purpose can be any compound that dissolves the maleimide compound only to a light degree and has miscibility with the solvent of the reaction mixture, and typical examples thereof include water, methyl alcohol, ethyl alcohol, 1-propyl alcohol, 2-propyl alcohol, 1-butyl alcohol, 2-butyl alcohol, tert-butyl alcohol, benzene, toluene, xylene, ethyl isobutyl ether, ethyl isopropyl ether, chloroform, chlorobenzene, and the like. Among them, water and methyl alcohol are preferred because they are easy to handle, inexpensive, and harmless to environmental health. The amount of precipitant used may be from 0.3 to 50 times the volume of the reaction mixture.

In order to further improve its purity, the maleimide compound thus obtained is usually subjected to an additional purification procedure. Specifically, the precipitate formed in the above-described manner is separated from the mother liquor. The resulting cake is dispersed again in water to form a slurry. This slurry is neutralized with a basic compound such as sodium carbonate, sodium hydrogen carbonate, or the like until its pH reaches a value of from 8.0 to 9.0. Thereafter, the precipitate is separated, washed several times with water and thoroughly with methyl alcohol, and then dried to obtain the desired maleimide compound. In this procedure, the neutralization of a slurry of the precipitate with a basic compound such as sodium carbonate, sodium hydrogen carbonate, or the like is not essential to the process of the present invention. In fact, a sufficient degree of purification can be achieved simply by washing the precipitate several times with water and then with an alcohol. However, if a slurry of the precipitate is neutralized with a basic compound, the desired maleimide compound is further purified as a result of synergistic effects. Specific examples of the alcohol used for washing purposes in the process of the present invention include methyl alcohol, ethyl alcohol, 1-propyl alcohol, 2-propyl alcohol, 1-butyl alcohol, 2-butyl alcohol, and the like. The amount of alcohol used may be from 1.1 to 30 times the weight of the precipitate. This washing with an alcohol also has the advantage that the time required for drying the maleimide compound thus obtained can be reduced.

The novel maleimide compounds (i.e. alkenylphenylmaleimide derivatives and linear dimers thereof) of the present invention are relatively low-molecular-weight compounds containing two or more double bonds in the molecule. They may be used alone or in combination with other suitable monomers or polymers to form a variety of thermosetting resins which can be converted to cured products having the so-called three-dimensional network. Such thermosetting resins comprising the maleimide compounds of the present invention are characterized by excellent heat resistance, good dimensional stability, and easy moldability, and can therefore be widely used in electrical and mechanical applications including impregnating varnishes, laminates, molding materials, coating materials, adhesives, and the like. In addition, the maleimide compounds of the present invention also have great utility and wide applications in those industrial fields (for example, agricultural chemicals and rubber chemicals) which require special functions. Moreover, owing to their characteristic properties such as high solubility in organic solvents, low melting point, and the like, the maleimide compounds of the present invention permit simplification of operating procedures and offer much saving in energy.

The present invention is further illustrated by the following examples. These examples are illustrative only and are not intended for purposes of limitation.

EXAMPLE 1

Maleic anhydride (43.2 g) was dissolved in 400 ml of acetone. While this solution was being kept at 20° C., 53.3 g of p-isopropenylaniline was slowly added thereto with stirring. The resulting reaction mixture was stirred at 20° C. for 1⅔ hours, so that it became a yellow slurry. Then, 0.8 g of cobalt acetate tetrahydrate, 14 g of triethylamine, and 50 g of acetic anhydride were added, with stirring, to the above slurry. After completion of the addition, the slurry was heated to 60° C. and stirred at that temperature for 2 hours, so that it became a clear brown solution. After this solution was cooled to room temperature, 40 ml of methyl alcohol was added thereto. The, the solution was slowly poured into 4,000 ml of vigorously stirred water. The precipitate so formed was separated by filtration and then washed with water, with an aqueous sodium carbonate solution, and thoroughly with water. Thereafter, the precipitate was dried at 60° C. under reduced pressure to obtain 81 g of product melting at 109°–117° C. Its yield was 95% based on the amount of p-isopropenylaniline used as the starting material. It was confined by infrared absorption spectroscopy, nuclear magnetic resonance spectroscopy, and elemental analysis that the product was N-p-isopropenylphenylmaleimide having the formula

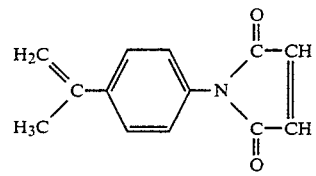

The analytical data were as follows.

| Infrared absorption spectrum: | |
|---|---|
| Group | Absorption Band |
| $\diagdown$C=O (carbonyl) | 1710 cm$^{-1}$ |
| —N$\diagup$ (imido) | 1765 cm$^{-1}$ |

| N.M.R. spectrum (in DMSO-D$_6$): | |
|---|---|
| Group | δ Value |
| —CH$_3$ | 2.12 |
| =CH$_2$ | 5.11, 5.45 |
| HC—<br>‖<br>HC— | 7.12 |

| | | | 7.28, 7.58 |
|---|---|---|---|

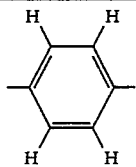

| Chemical composition: | C | H | N |
|---|---|---|---|
| Calculated Value (%) | 73.25 | 5.20 | 6.57 |
| Found Value (%) | 73.12 | 5.24 | 6.49 |

EXAMPLE 2

N,N'-(1-methylene-3,3-dimethyltrimethylenedi-p-phenylene)-bismaleamic acid (46 g) having the formula

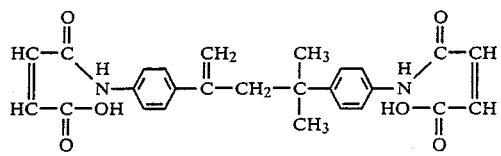

was dispersed in 300 ml of acetone to form a slurry. To this slurry were added, with stirring, 0.8 g of cobalt acetate tetrahydride and 14 g of triethylamine, and then 26 g of acetic anhydride. The resulting reaction mixture was heated to 60° C., kept at that temperature for 2½ hours, and then cooled to room temperature. To this reaction mixture were added 20 ml of methyl alcohol and then 1,500 ml of water. The precipitate so formed was separated by filtration and dispersed again in water, when was then adjusted to pH 9.0 by the addition of sodium carbonate. Thereafter, the precipitate was washed thoroughly with water. Finally, the precipitate was washed with 40 g of methyl alcohol and then dried at 50° C. under reduced pressure to obtain 33 g of product melting at 148°–151° C. Its yield was 77% based on the amount of bismaleamic acid used as the starting material. It was confirmed by infrared absorption spectroscopy, nuclear magnetic resonance spectroscopy, and elemental analysis that the product was N,N'-(1-methylene-3,3-dimethyltrimethylenedi-p-phenylene)-bismaleimide having the formula

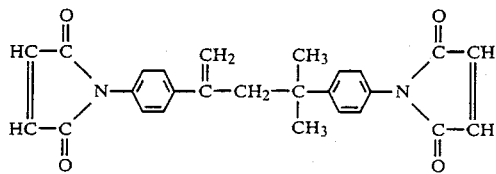

The analytical data were as follows.

| Infrared absorption spectrum: | |
|---|---|
| Group | Absorption Band |
| $\diagup$C=O (carbonyl) | 1700 cm$^{-1}$ |
| —N$\diagup$ (imido) | 1762 cm$^{-1}$ |

| N.M.R. spectrum: | |
|---|---|
| Group | δ Value |
| —CH$_3$ | 1.24 |
| —CH$_2$— | 2.86 |
| =CH$_2$ | 4.90, 5.22 |
| HC—<br>\|<br>HC— | 7.07 |
| 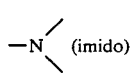 | 7.12, 7.35 |

| Chemical composition: | C | H | N |
|---|---|---|---|
| Calculated Value (%) | 73.24 | 5.20 | 6.57 |
| Found Value (%) | 73.19 | 5.21 | 6.54 |

EXAMPLE 3

Maleic anhydride (43 g) was dissolved in 250 ml of acetone. While this solution was being kept at 18° C., 53 g of 2,4-di(p-amino-phenyl)-4-methyl-2-pentene was slowly added thereto with stirring. The resulting reaction mixture was stirred at 18° C. for 2½ hours to form N,N'-(1-methyl-3,3-dimethyl-1-propenylenedi-p-phenylene)-bismaleamic acid having the formula

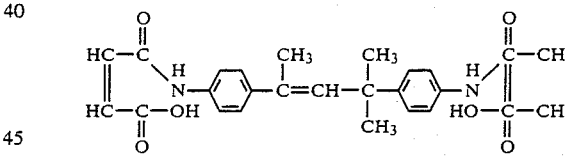

At this time, the reaction mixture was a yellow slurry. Then, 0.5 g of cobalt acetate tetrahydrate, 10 g of triethylamine, and 50 g of acetic anhydride were added, with stirring, to the above slurry. After completion of the addition, the slurry was heated to 61° C. and stirred at that temperature for 8 hours, so that it became a clear brown solution. This solution was cooled to room temperature and, thereafter, worked up in the same manner as described in Example 1. However, the amount of methyl alcohol added to the solution was 80 ml and the amount of water into which the solution was poured was 7,000 ml. As a result, there was obtained 80 g of product melting at 99°–110° C. Its yield was 94% based on the amount of diamine used as the starting material. It was confirmed by infrared absorption spectroscopy, nuclear magnetic resonance spectroscopy, and elemental analysis that the product was N,N'-(1-methyl-3,3-dimethyl-1-propenylenedi-p-phenylene)-bismaleimide having the formula

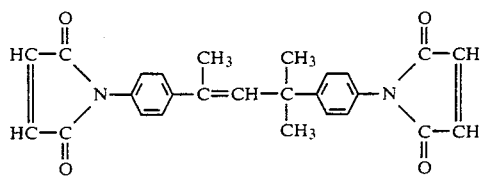

The analytical data were as follows.

| Infrared absorption spectrum: | |
|---|---|
| Group | Absorption Band |
| $\diagup\!\!\!\!\diagdown\!\!\text{C}=\text{O}$ (carbonyl) | 1710 cm$^{-1}$ |
| $-\text{N}\diagup\!\!\!\!\diagdown$ (imido) | 1770 cm$^{-1}$ |

| N.M.R. spectrum: | |
|---|---|
| Group | δ Value |
| —CH$_3$ | 1.53 |
| —CH= | 6.21 |
| HC—<br>‖<br>HC— | 7.11 |
| (phenylene H's) | 7.25, 7.53 |

| Chemical composition: | C | H | N |
|---|---|---|---|
| Calculated Value (%) | 73.24 | 5.20 | 6.57 |
| Found Value (%) | 73.20 | 5.18 | 6.60 |

EXAMPLE 4

Maleic anhydride (50 g) was dissolved in 120 ml of acetone. While this solution was being kept at 15° C., 83 g of 2-chloro-4-isopropenylaniline was added thereto. The resulting reaction mixture was stirred at 15° C. for 2 hours. Then, 0.9 g of cobalt acetate tetrahydrate, 16 g of triethylamine, and 57 g of acetic anhydride were added, with stirring, to the above reaction mixture. Thereafter, the reaction mixture was heated to 60° C, stirred at that temperature for 2½ hours, and then cooled to room temperature. After the addition of 50 ml of methyl alcohol, the reaction mixture was slowly poured into 2,000 ml of vigorously stirred water. The precipitate so formed was separated by filtration and then washed with water, with an aqueous sodium carbonate solution, and thoroughly with water. Finally, the precipitate was washed with 150 ml of methyl alcohol and then dried at 50° C under reduced pressure to obtain 109 g of N-(2-chloro-4-isopropenylphenyl)maleimide in a 89% yield. The analytical data were as follows.

| | C | H | N | Cl |
|---|---|---|---|---|
| Calculated Value (%) | 63.04 | 4.07 | 5.66 | 14.31 |
| Found Value | 62.95 | 4.09 | 5.61 | 14.28 |

EXAMPLE 5

The procedure of Example 4 was repeated except that the 2-chloro-4-isopropenylaniline was replaced by 73.6 g of 4-methyl-2,4-bis(3'-methyl-4'-aminophenyl)-1-pentene having the formula

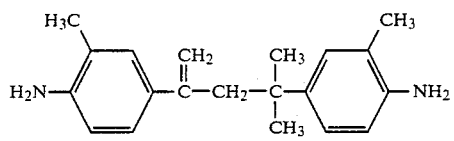

As a result, there was obtained 103 g of product in a 91% yield. It was confirmed by infrared absorption spectroscopy, nuclear magnetic resonance spectroscopy, and elemental analysis that the product was N,N'-[1-methylene-3,3-dimethyltrimethylenebis(3'-methyl-1',4'-phenylene)]bismaleimide having the formula

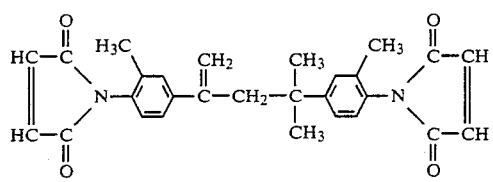

The analytical data were as follows:

| | C | H | N |
|---|---|---|---|
| Calculated Value (%) | 73.99 | 5.77 | 6.16 |
| Found Value (%) | 73.87 | 5.72 | 6.14 |

EXAMPLE 6

The procedure of Example 4 was repeated except that the 2-chloro-4-isopropenylaniline was replaced by 73.6 g of 2-methyl-4-isopropenylaniline. As a result, there was obtained 101 g of product in an 89% yield. It was confirmed by infrared absorption spectroscopy, nuclear magnetic resonance spectroscopy, and elemental analysis that the product was N-(2-methyl-4-isopropenylphenyl)-maleimide. The analytical data were as follows:

| | C | H | N |
|---|---|---|---|
| Calculated Value (%) | 73.99 | 5.77 | 6.16 |
| Found Value (%) | 73.91 | 5.69 | 6.13 |

What is claimed is:
1. Process for the preparation of an alkenylphenylmaleimide having the formula:

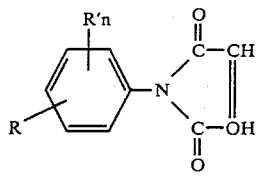

(I)

wherein R is alkenyl having 3 to 12 carbon atoms, R' is hydrogen, halogen or alkyl having 1 to 4 carbon atoms, and n is a whole number of 1 to 4, or a bismaleimide having the formula:

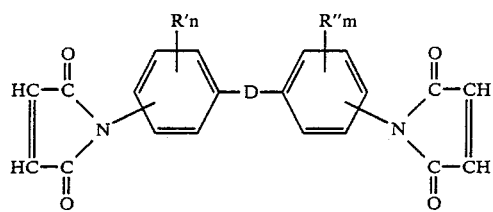

(II)

wherein R' and R" can be the same or different and are hydrogen, halogen or straight-chain or branched alkyl having 1 to 4 carbon atoms, n and m are whole numbers of 1 to 4, and D is an ethylenically unsaturated hydrocarbon group having 6 to 24 carbon atoms, which comprises the step of effecting reaction of an alkenylphenylmaleic acid derivative having the formula:

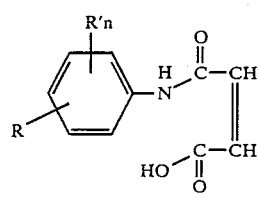

(III)

wherein R, R' and n are as defined above for formula (I), or a linear dimer of like or different alkenylphenylmaleamic acid derivatives having the formula:

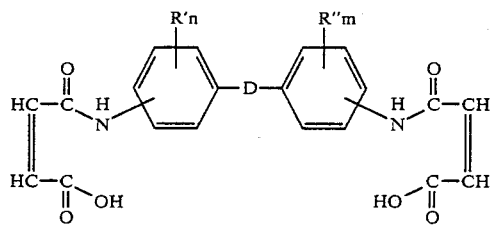

(IV)

wherein R', R", n, m and D are as defined above for formula (II), with at least one dehydrating agent which is a carboxylic acid anhydride in the presence of a tertiary amine, an organic solvent and a catalyst, the catalyst being selected from the group consisting of: sodium sulfate, sodium carbonate, sodium phosphate, potassium sulfate, potassium carbonate, potassium phosphate, lithium sulfate, lithium carbonate, lithium phosphate, iron sulfate, iron carbonate, iron phosphate, nickel sulfate, nickel carbonate, nickel phosphate, cobalt sulfate, cobalt carbonate, cobalt phosphate, copper sulfate, copper carbonate, copper phosphate, manganese sulfate, manganese carbonate, manganese phosphate, sodium nitrate, sodium acetate, sodium butyrate, potassium nitrate, potassium acetate, potassium butyrate, lithium nitrate, lithium acetate, lithium butyrate, iron nitrate, iron acetate, iron butyrate, nickel nitrate, nickel acetate, nickel butyrate, cobalt nitrate, cobalt acetate, cobalt butyrate, manganese nitrate, manganese acetate, manganese butyrate, copper nitrate, copper acetate, copper butyrate, sodium pyrophosphate, nickel pyrophosphate, potassium pyrophosphate, lithium pyrophosphate, manganese pyrophosphate, iron pyrophosphate, copper pyrophosphate, acetylacetone complex of iron, acetylacetone complex of nickel, acetylacetone complex of cobalt, acetylacetone complex of copper and acetylacetone complex of manganese, to form the corresponding alkenylphenylmaleimide or bismaleimide.

2. The process as claimed in claim 1 the dehydrating agent is acetic anhydride.

3. The process as claimed in claim 1 wherein the catalyst is used in an amount of from 0.001 to 1.2 moles per mole of the alkenylphenylmaleamic acid derivative or the linear dimer thereof.

4. The process as claimed in claim 1 wherein the tertiary amine is selected from the group consisting of a trialkylamine having alkyls having 3 to 20 carbon atoms, N,N-diethylcyclohexylamine, N,N-dimethylbenzylamine, N-methylpiperidine, 1,4-diazabicyclo[2.2.2]octane, 1,8-diazabicyclo[5.4.0]7-undecene and N-methylmorpholine.

5. The process as claimed in claim 4 wherein the tertiary amine is triethylamine.

6. The process as claimed in claim 1 wherein the teritary amine is used in an amount of from 0.01 to 1.1 moles per mole of the alkenylphenylmaleamic acid derivative or the linear dimer thereof.

7. The process as claimed in claim 1 wherein the organic solvent is selected from the group consisting of chloroform, methylene chloride, carbon tetrachloride, acetone, methyl ethyl ketone, cyclohexanone, formic acid, acetic acid, butyric acid, methyl acetate, theyl acetate, butyl acetate, methanol, ethanol, propanol, ether, dioxane, tetrahydrofuran, 1-ethoxyethanol, 1-methoxyethanol, cyclohexane, benzene, toluene, xylene, mesitylene, chlorobenzene, cresol, dichlorobenzene, acetonitrile, pyridine, N,N-dimethyl acetamide, N,N-dimethylformamide, N-methyl-2-pyrolidone, N-methylcaprolacetam, dimethylsulfoxide and tetramethylene sulfone.

8. The process as claimed in claim 7 wherein the organic solvent is acetone, methyl ethyl ketone, tetrahydrofuran or N,N-dimethylformamide.

9. The process as claimed in claim 1 wherein the reaction is carried out at a temperature of from 30° to 80° C.

10. The process as claimed in claim 1 which further comprises the steps of, after completion of the reaction, adding an aliphatic alcohol to the reaction mixture and then separating the desired product with the aid of a precipitant selected from the group consisting of water, methanol, ethanol, propanol, isopropanol, 1-butanol, 2-butanol, tert-butylalcohol, benzene, toluene, xylene, ethyl-isopropyl ether, ethyl isobutyl ether, chloroform and chlorobenzen.

11. The process as claimed in claim 10 wherein the alcohol is an aliphatic alcohol having 1 to 4 carbon atoms.

12. The process as claimed in claim 11 wherein the alcohol is methanol.

13. The process as claimed in claim 10 wherein the alcohol is used in an amount of from 0.05 to 200 g per 100 g of the reaction mixture.

14. The process as claimed in claim 10 wherein the alcohol is added to the reaction mixture having a temperature of from 5° to 40° C.

15. The process as claimed in claim 10 wherein the precipitant is water.

16. The process as claimed in claim 1 wherein the alkenylphenylmaleamic acid derivative is p-isopropenylphenylmaleamic acid.

17. The process as claimed in claim 1 wherein the linear dimer of like or different alkenylphenylmaleamic acid derivatives is a linear dimer of p-isopropenylphenylmaleamic acid.

18. The process as claimed in claim 1 wherein the linear dimer of like or different alkenylphenylmaleamic acid derivatives are N,N'-(1-methylene-3,3-dimethyltrimethylenedi-p-phenylene)-bismaleamic acid or N,N'-(1-methyl-3,3-dimethyl-1-propylenedi-p-phenylene) bismaleamic acid.

19. The process as claimed in claim 1 wherein the catalyst is a hydrated or unhydrated carboxylic acid salt of sodium cobalt or nickel.

20. The process as claimed in claim 1 wherein the catalyst is a hydrated or unhydrated sodium acetate, cobalt (II) acetate or nickel acetate.

* * * * *